(12) United States Patent
Lovich et al.

(10) Patent No.: US 8,562,586 B2
(45) Date of Patent: Oct. 22, 2013

(54) DEVICES AND SYSTEMS FOR LOCAL DELIVERY OF INOTROPIC AGENTS TO THE EPICARDIUM

(75) Inventors: Mark Lovich, Brookline, MA (US); Elazer Edelman, Brookline, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 1064 days.

(21) Appl. No.: 12/547,959

(22) Filed: Aug. 26, 2009

(65) Prior Publication Data
US 2010/0057039 A1    Mar. 4, 2010

Related U.S. Application Data

(60) Provisional application No. 61/227,253, filed on Jul. 21, 2009, provisional application No. 61/091,780, filed on Aug. 26, 2008.

(51) Int. Cl.
*A61M 31/00* (2006.01)
*A61M 1/00* (2006.01)

(52) U.S. Cl.
USPC .... 604/502; 604/93.01; 604/151; 604/288.04

(58) Field of Classification Search
USPC .............. 604/500, 502, 93.01, 151, 604/288.01–288.04; 424/423, 427
See application file for complete search history.

(56) References Cited

U.S. PATENT DOCUMENTS 3,987,200 A    10/1976 Tuttle et al.
(Continued)

FOREIGN PATENT DOCUMENTS

| EP | 1 588 736 A2 | 10/2005 |
|---|---|---|
| WO | WO 99/36538 A1 | 7/1999 |
| WO | WO 02/24159 A2 | 3/2002 |
| WO | WO 2005/118069 A1 | 12/2005 |

OTHER PUBLICATIONS

Haider et al., "Improved Cardiac Performance and Reduced Pulmonary Vascular Constriction by Epinephrine Administration via a Left Atrial Catheter in Cardiac Surgical Patients," Journal of Cardiothoracic and Vascular Anesthesia, vol. 7, No. 6, 1993, pp. 684-687.

(Continued)

*Primary Examiner* — Kevin C Sirmons
*Assistant Examiner* — Imani Hayman
(74) *Attorney, Agent, or Firm* — Sutherland Asbill & Brennan LLP (57) ABSTRACT

Devices and methods are provided for delivery of a positive inotropic agent to the heart of a patient in need thereof. An epicardial patch includes (i) a backing layer which is impermeable to the positive inotropic agent; and (ii) a drug release layer attached to the backing layer and including the positive inotropic agent and a polymeric membrane material. The polymeric membrane material provides controlled release of the positive inotropic agent to the epicardium to a region of the myocardium and in an amount effective to increase contractility. At least one of the backing layer or the drug release layer includes a tissue coupling portion for affixing the epicardial patch to an area of the epicardial surface. The epicardial patch is dimensioned and compliant to substantially avoid impeding myocardial functionality when affixed to the area of the epicardial surface.

24 Claims, 7 Drawing Sheets

(56) References Cited

U.S. PATENT DOCUMENTS

| | | | |
|---|---|---|---|
| 4,637,815 | A | 1/1987 | Lemole |
| 5,387,419 | A | 2/1995 | Levy et al. |
| 5,900,433 | A | 5/1999 | Igo et al. |
| 6,296,630 | B1 | 10/2001 | Altman et al. |
| 6,726,920 | B1 | 4/2004 | Theeuwes et al. |
| 2002/0055705 | A1 | 5/2002 | Talpade |
| 2002/0150622 | A1 | 10/2002 | Philbrook et al. |
| 2002/0188325 | A1 | 12/2002 | Hill et al. |
| 2003/0036773 | A1 | 2/2003 | Whitehurst et al. |
| 2003/0064088 | A1* | 4/2003 | Carvalho et al. ............ 424/423 |
| 2003/0124503 | A1 | 7/2003 | Olivencia-Yurvati et al. |
| 2004/0034272 | A1 | 2/2004 | Diaz et al. |
| 2004/0039063 | A1 | 2/2004 | Wink et al. |
| 2004/0162346 | A1 | 8/2004 | Lopaschuk et al. |
| 2004/0199209 | A1 | 10/2004 | Hill et al. |
| 2005/0004428 | A1 | 1/2005 | Cox et al. |
| 2005/0267556 | A1 | 12/2005 | Shuros et al. |
| 2007/0021358 | A1 | 1/2007 | Edelman et al. |

OTHER PUBLICATIONS

Hideaki Takai et al., "The Efficacy of Low Prime Volume Completely Closed Cardiopulmonary Bypass in Coronary Artery Revascularization," pp. 178-182, Ann Thorac Cardiovascular Surgery, vol. 10, No. 3, 2004.

Fullerton et al., "Hemodynamic Advantage of Left Atrial Epinephrine Administration after Cardiac Operations," pp. 1263-1266, 1993.

Skelding et al., "Resolution of Refractory No-Reflow with Intracoronary Epinephrine," pp. 306-309, 2002.

Maria Helena L. Souza et al., "Weaning from Cardiopulmonary Bypass," Virtual Textbook of Extracorporeal Technology, 1999. Available at <http:perfline.com/textbook/local/weaning0399.html>.

Wilson S. Colucci, "Observations on the Intracoronary Administration of Milrinone and Dobutamine to Patients with Congestive Heart Failure," The American Journal of Cardiology, Jan. 1989, pp. 17A-22A.

PCT Search Report for International Application No. PCT/US2006/020252 with an International Filing date of May 25, 2006.

Seguin et al., "Effects of Epinephrine Compared with the Combination of Dobutamine and Norepinephrine on Gastric Perfusion in Septic Shock," Clinical Pharmacology & Therapeutics, pp. 381-388, May 2002.

Tinker et al., "Dobutamine for Inotropic Support During Emergence from Cardiopulmonary Bypass," The Journal of Anesthesiology, pp. 281-286, vol. 44, No. 4, Apr. 1976.

Von Degenfeld et al., "Targeting of Dobutamine to Ischemic Myocardium without Systemic Effects by Selective Suction and Pressure-Regulated Retroinfusion," Cardiovascular Research, pp. 233-240, vol. 35, 1997.

Definition of "Inotropic," Stedman's Medical Dictionary 27th Edition. Available at http://www.thomsonhc.com/pdrel/librarian/ND_T/PDRel/ND_C...al/PFPUI/1T1DjrY2tobB4C/PFActionId/pf.PrintReadyDocument6/14/2008.

Definition of "Inotrope," From Wikipedia. Available at http://en.wikipedia.org/wiki/Inotrope (1 of 4).

\* cited by examiner

Comparison of Effect of Dobutamine Release from
Patch (P) and IV on Systemic Vascular Resistance

FIG. 5

Comparison of Potency and Efficacy of Dobutamine
Release from Patch (P) and IV Infusion

DEVICES AND SYSTEMS FOR LOCAL DELIVERY OF INOTROPIC AGENTS TO THE EPICARDIUM

CROSS-REFERENCE TO RELATED APPLICATIONS

Priority is claimed to U.S. Provisional Application No. 61/091,780, filed Aug. 26, 2008, and to U.S. Provisional Application No. 61/227,253, filed Jul. 21, 2009. The applications are incorporated by reference herein in their entirety.

TECHNICAL FIELD

The present disclosure relates generally to devices, systems, and methods for local, controlled administration of a drugs to the heart of a patient in need thereof, and more particularly to devices, systems, and methods for delivery of drugs, such as inotropic agents, directly to the epicardium.

BACKGROUND

Myocardial failure is a major source of morbidity and mortality. Nearly one out of every 56 Americans (approximately 1.8 percent of the population) suffer from some forms of myocardial failure. Patients in acute heart failure often are supported on systemic administration of medications to increase the force of the myocardial contraction. Such agents generally are referred to as inotropes, and often are given in intensive care units and operating rooms to increase cardiac output and organ perfusion.

Pharmacologic inotropic agents generally are classified by their mechanisms of action. Three examples of categories are sympathomimetics, phophodiesterase inhibitors, and calcium sensitizers. Other inotropes also are known and work by distinctly different mechanisms. Although each of these compounds may be used to increase the inotropic state of the heart, the amount administered is often limited in order to minimize undesirable systemic side effects. Frequently the infusion of additional agents is required to counteract side effects of systemically delivered inotropic drugs.

For example, dopamine dosing is limited by the increase in the rate and irritability of electrical excitation of the heart that accompanies a desired inotropic effect. Ventricular irritability may be so severe, however, that powerful anti-arrhythmic agents may be required to attempt to stabilize the myocardial cells and prevent these life threatening conditions. Administration of milrinone, a phosphodiesterase inhibitor that increases intracellular cyclicAMP (an intracellular signaling molecule that increases intropy), may result in dilation of the arterioles and causes systemic vasodilation and hypotension. As a result, a vasoconstricting agent may need to be co-administered.

Controlled release drug delivery from devices implanted about or injected into cardiac tissue has been variously described. See, e.g., U.S. Patent Application Publication No. 2008/0095824 A1 to Struijker-Boudier et al. Many of these delivery schemes involve injection into the myocardium or other significant violation of the myocardial tissue, which generally is undesirable but is particularly so in a heart with poor myocardial contractility.

Furthermore, some localized delivery strategies are ineffective for improving myocardial contraction, for example, because the delivery strategy only provides drug to a small localized fraction of the myocardial cells and the inotropic agents are not delivered to a large enough surface area of myocardial tissue, in an effective amount throughout the area. For example, an injection or other pinpoint delivery does not deliver the drug evenly to a large, but select, region of the myocardium.

Similarly, other local delivery schemes, such as infusion of a solution comprising an inotropic agent via a catheter into the pericardial space, also may fail to target delivery of the inotropic agent to the particular areas of the myocardium that would improve contractility and/or may fail to provide effective tissue levels of the drug at those required sites. More specifically, an inotropic agent introduced into the pericardial space in this way would be diluted in the pericardial fluid that bathes the outer surface of heart (the epicardium), thereby undesirably inhibiting the ability to target specific portions of myocardial tissue where the agent is needed (as pericardial fluid potentially carries the drugs to areas of the myocardium that would not be beneficial or may clear the drug away from the heart and into the lymphatic system) and decreasing drug delivery to the tissues that are targeted (as dilution of the inotropic agent in the pericardial fluid undesirably decreases the concentration of the drug at the epicardial surface which reduces, according to mass transport kinetics, the rate at which the drug can diffuse into the tissue).

In light of the foregoing limitations associated with current approaches to administration of inotropic agents and to the administration of drugs to the myocardium, there remains a need for new devices, systems, and methods for local delivery of inotropic agents to the myocardium. In particular, devices and methods are needed to achieve effective myocardial tissue levels of the inotropic agent while reducing the systemic levels of the inotropic agent, without violating the myocardial tissues. It would also be desirable to provide sustained release systems able to passively deliver effective amounts of inotropic agent to the myocardium over sustained periods, for example, for several days or weeks following cardiac surgery or for several months, for use with ambulatory patients and patients having chronic heart conditions.

BRIEF SUMMARY

In one aspect, an epicardial patch is provided for delivery of a positive inotropic agent to the heart of a patient. The epicardial patch comprises a backing layer which is impermeable to the positive inotropic agent, and a drug release layer attached to the backing layer and comprising the positive inotropic agent and a polymeric membrane material. Upon placement of the epicardial patch onto a portion of the epicardial surface of the heart, the polymeric membrane material provides controlled release of the positive inotropic agent to the epicardium to a region of the myocardium and in an amount effective to increase contractility. At least one of the backing layer or the drug release layer comprises a tissue coupling portion for affixing the epicardial patch to an area of the epicardial surface. The epicardial patch is dimensioned and compliant to substantially avoid impeding myocardium functionality when affixed to the area of the epicardial surface.

In some embodiments, the positive inotropic agent and the polymeric membrane material are combined in the drug release layer in a monolithic, matrix form. In other embodiments, the positive inotropic agent in the drug release layer is disposed in at least one discrete reservoir defined between the backing layer and the polymeric membrane material. In certain embodiments, the discrete reservoir is fillable, or refillable, after affixation to the epicardial surface. In certain embodiments, the epicardial patch further includes a fluid connection element for connecting a device to a fluid source for refilling the reservoir.

In some embodiments, the epicardial patch further comprising an array of microneedles which facilitate affixing of the patch to the epicardial surface and/or facilitate control of release of the positive inotropic agent to the epicardium. Further, in some embodiments, the tissue coupling portion comprises an adhesive material.

In some embodiments, the epicardial patch is resorbable. In certain embodiments, the patch is resorbable over a period between about 7 and about 180 days.

In some embodiments, the positive inotropic agent comprises a sympathomimetic agent, a phosphodiesterase inhibitor, a calcium sensitizer, or a combination thereof. In certain embodiments, the sympathomimetic agent is selected from the group consisting of epinephrine, norepinephrine, dobutamine, isoproterenol, salbutamol, salmeterol, terbutaline, phenylephrine, ephedrine, clonidine, dopamine, and any combination thereof. In certain other embodiments, the phosphodiesterase inhibitor is selected from the group consisting of milrinone, enoximone, amrinone, and any combination thereof. In certain embodiments, the calcium sensitizer is selected from the group consisting of levosimendan, pimobendan, and any combination thereof.

In some embodiments, the polymeric membrane material comprises a hydrogel. In certain embodiments, the polymeric membrane material comprises a poly(lactic-co-glycolic) acid, a polylactide; a poly(orthoester), a poly(aminoester), a polyethylene glycol, a polyanhydride, a polyorganophosphazene, a polyacrylate, or a combination thereof. In certain embodiments, the polymeric membrane material comprises micro-perforations.

In some embodiments, the epicardial patch provides release of the inotropic agent at therapeutically effective amounts for 7 days, 14 days, 30 days, 60 days, 90 days, or 100 days. In certain embodiments, release is substantially zero-order over the period of release.

In some preferred embodiments, upon the placement of the pericardial patch onto the portion of the epicardial surface of the heart, the epicardial patch is configured to restrict the release of the inotropic agent from the drug release layer such that only a unidirectional release of the inotropic agent from the drug release layer is permitted, wherein the direction of the unidirectional release is toward the region of the myocardium. Further, in some preferred embodiments, the epicardial patch is dimensioned to cover a sufficient area of the epicardial surface of the heart to deliver a therapeutically effective amount of the positive inotropic agent to the myocardium at a released dose of about 1.0 mcg/kg/min dobutamine, about 0.05 mcg/kg/min levosimendan, or about 0.1 mcg/kg/min milrinone. Intravenous infusion systems, on the other hand, typically require dosages of at least 2 mcg/kg/min dobutamine, 0.1 mcg/kg/min levosimendan, or 0.5 mcg/kg/min milrinone to have therapeutic effect on contractility. Accordingly, the drug delivery system of the present invention may be therapeutic at approximately one-half to one-third of the dosage rate of conventional intravenous infusion systems.

In another aspect, a drug delivery system is provided for delivery of a positive inotropic agent to the heart of a patient. The drug delivery system comprises a reservoir device housing a liquid formulation, an implantable epicardial patch affixable to an area of the epicardial surface of the heart, and a soft catheter having a first end connected to the reservoir, an opposed second end connected to the epicardial patch, the tube being effective to transport the liquid formulation from the reservoir to the epicardial patch. The liquid formulation comprises an inotropic agent, and the epicardial patch comprises a backing layer which is impermeable to the inotropic agent. The patch provides controlled release of the positive inotropic agent over the surface of a region of the myocardium and in an amount effective to increase contractility.

In some embodiments, the reservoir device is wholly implantable within the patient. In certain embodiments, the reservoir device is adapted for subcutaneous implantation. In other embodiments, the reservoir device is adapted for external placement on or near the patient.

In some embodiments, the patch or reservoir device comprises a pump. In certain embodiments, the pump is a peristaltic pump, an osmotic pump, or a MEMS (microelectromechanical systems) pump. In some embodiments, the drug delivery device further comprises control and telemetry circuitry and a power source for controlling flow of the liquid formulation from the reservoir device. In certain embodiments, the control and telemetry circuitry and power source are packaged together in a housing with the reservoir device.

In some preferred embodiments, the epicardial patch further comprises a drug release layer attached to the backing layer, which, upon placement of the epicardial patch onto a portion of the epicardial surface of the heart, provides controlled release of the positive inotropic agent to the epicardium to the region of the myocardium and in the amount effective to increase contractility. In some preferred embodiments, at least one of the backing layer or the drug release layer comprises a tissue coupling portion for affixing the epicardial patch to an area of the epicardial surface. Further, in some embodiments, the epicardial patch is dimensioned and compliant to substantially avoid impeding myocardium functionality when affixed to the area of the epicardial surface.

In some embodiments, upon the placement of the pericardial patch onto the portion of the epicardial surface of the heart, the epicardial patch is configured to restrict the release of the inotropic agent from the drug release layer such that only a unidirectional release of the inotropic agent from the drug release layer is permitted, wherein the direction of the unidirectional release is toward the region of the myocardium. Further, in some preferred embodiments, the epicardial patch is dimensioned to cover a sufficient area of the epicardial surface of the heart to deliver a therapeutically effective amount of the positive inotropic agent to the myocardium at a released dose of about 1.0 mcg/kg/min dobutamine, about 0.05 mcg/kg/min levosimendan, or about 0.1 mcg/kg/min milrinone.

In another aspect, a method of treating a patient's heart is provided. The method includes the steps of: (1) providing a positive inotropic agent; (2) providing an implantable epicardial patch affixable to an area of an epicardial surface of the heart, the epicardial patch comprising a backing layer which is impermeable to the inotropic agent; (3) placing the epicardial patch onto the epicardial surface of the heart; and (4) administering the positive inotropic agent from the epicardial patch to the epicardium to a region of the myocardium in an amount effective to increase contractility.

DETAILED DESCRIPTION

Improved drug delivery devices, systems, and methods have been developed for delivering an inotropic agent to the myocardium via local drug release directed to the epicardium, meeting one or more of the needs in the art described above.

In U.S. Patent Application Publication No. 2007/0021358 A1, various methods and devices for localized delivery of inotropic agents to the heart are described. Improved devices and methods are now described herein for effectively delivering inotropic agents, particularly for directed delivery and sustained release, without violating the myocardial tissue structure and function.

Previously described delivery schemes may be unsuitable or ineffective for enhancing myocardial contraction. For example, in one basic approach, a fluid drug is feed into the pericardial sac via infusion using a catheter. This infusion approach has been found by the applicants to be ineffective, at least for administration of certain inotropic agents.

In one aspect, a drug delivery device is provided that comprises a patch adapted for placement on the epicardial surface of the heart, which provides localized delivery of an inotropic agent to a specific region of the heart. The patch provides control over the direction, rate, duration, and area of drug release.

I. The Drug Delivery Patch

A drug delivery patch is provided for localized delivery of an inotropic agent to the heart. The patch generally may be provided in any configuration or geometry that would be suitable for a given cardiac use. For example, the patch may be adapted for delivery of an inotropic agent over an extended period of time—several hours (e.g., greater than 8 hours), days (e.g., greater than 3 days), or several weeks. Accordingly, embodiments of the present invention may be particularly suited for use in patients suffering from chronic heart failure.

In one embodiment, a drug delivery patch comprises a backing layer, a drug delivery layer, and a drug reservoir comprising an inotropic agent. The patch is of a shape and a size such that it is suitable for epicardial delivery of an inotropic agent.

A. The Patch

Generally described, the patch comprises a backing layer, a drug delivery layer proximate to the backing layer, and a drug reservoir comprising an inotropic agent. The backing layer is generally substantially impermeable to the inotropic agent, such that it prevents or impedes diffusion of the inotropic agent away from the desired delivery site. For example, the term "substantially impermeable to the positive inotropic agent" includes permitting less than 10%, preferably less than 5%, and more preferably less that 1%, of the inotropic agent released by the patch to diffuse through the backing layer.

(i) The Patch Structure

The rate of drug delivery to the delivery site may be controlled using methods known to those skilled in the art. In one embodiment the drug delivery layer comprises a diffusion-controlling material. In one embodiment the patch further comprises a separate diffusion-controlling layer proximate to the drug delivery layer.

The patch may be provided in any configuration that is suitable for controlling the direction and rate of delivery of the inotropic agent to the heart while still being sufficiently flexible so that the patch does not interfere with the heart structure and function. For example, the patch may be any suitable shape and size suitable for epicardial delivery of a drug. The patch is dimensioned, for example, to have an tissue interface area large enough to cover a desired portion of the epicardium while also being sufficiently thin so that it is disposed on the epicardium within the pericardial sac. In one embodiment, the patch has a thickness in the range of about 0.5 mm to about 5 mm. Preferably, the patch is dimensioned and configured to cover a surface area of at least about 12 cm² up to about 100% of the ventricular epicardial surface of the heart. In one embodiment, the patch is in the form of sleeve, which may or may not be elastic, in which the heart may be fittingly accommodated, the sleeve covering from about 80% to 100% (e.g., 90% to 99%) of the ventricular epicardial surface.

Figure 1:
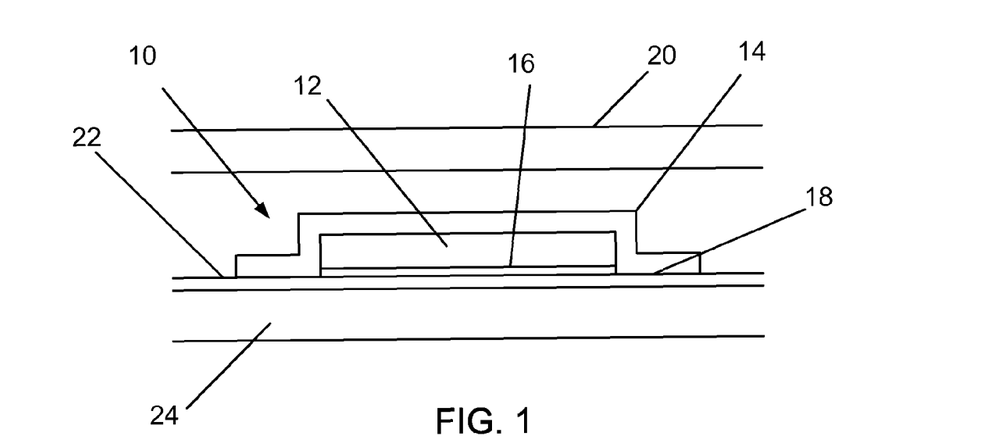
FIG. 1 is a side section view, illustrating one embodiment of an epicardial patch placed on an epicardial surface with a reservoir integral to the epicardial patch.

FIG. 1 illustrates an epicardial patch 10 placed on an epicardial surface 22 according to one or more embodiments of the present invention. The epicardial patch 10 comprises a backing layer 14 and a drug release layer which, in the present embodiment, comprises a drug reservoir 12 and a diffusion control layer 16. The drug reservoir 12 contains a predesignated volume of a drug to be delivered to the myocardial tissue 24 via the epicardial surface 22 such as a positive inotropic agent. The diffusion control layer 16 comprises a material that is permeable to the drug contained in the drug reservoir 12. The backing layer 14 is impermeable to the drug. As such, upon the placement of the epicardial patch 10 onto the epicardial surface 22, the epicardial patch 10 is advantageously configured to restrict the release of the drug from the drug release layer such that only a unidirectional release of the inotropic agent from the drug release layer is permitted (i.e., in a direction toward the myocardial tissue 24). Such a structure advantageously prevents the drug contained within drug reservoir 12 from diffusing directly into the fluid of the pericardium 20 and allows the drug to directly target and focus its effect on the relevant portion of the myocardial tissue 24 without exposing other portions of the heart to the drug.

A tissue coupling portion, such as a layer of adhesive, is provided on a bottom surface 18 of the backing polymer 14 to enable affixation of the epicardial patch 10 to the epicardial surface 22. Adhesive may also be provided on the bottom surface of the diffusion control layer 16 (i.e., the surface of the diffusion control layer 16 contacting the epicardial surface 22) if the adhesive is permeable to the drug contained in the drug reservoir 12. The epicardial patch 10 is dimensioned and compliant to substantially avoid impeding myocardium functionality when affixed to the epicardial surface 22.

(ii) The Drug Reservoir

The drug reservoir may be refillable or non-refillable. In one embodiment, the drug reservoir is provided to the physician in an initially filled formed. Alternatively, the drug reservoir may be filled following implantation. Desirably, the drug reservoir is refillable such that the device may be used for delivery of the inotropic agent to the heart over an extended period, e.g., for several days or weeks, such as in the case where the drug therapy should continue in cases of certain heart conditions (e.g., chronic heart failure). In one embodiment, the drug reservoir is disposed within or adjacent to the drug delivery layer. The drug reservoir may be refilled using any means suitable. For example, in one embodiment the drug reservoir is refilled by injection of the inotropic agent directly into the drug reservoir. In another embodiment, the device further comprises a catheter having a distal end and a proximal end, the proximal end being fluidly connected to the drug reservoir and the distal end being easily accessible for refilling the drug reservoir with the inotropic agent.

In another embodiment, the device optionally may further include a second drug reservoir external to the patch and remotely located from the patch. In one embodiment, the drug reservoir is operably connected to the patch via a catheter such that the patch is connected to the catheter at its proximal end and the drug reservoir is connected to the catheter at its distal end. In one embodiment, the drug reservoir is implanted subcutaneously. In another embodiment, the drug reservoir is implanted in an intra-peritoneal space (i.e., the peritoneal cavity). In still other embodiments, the drug reservoir is implanted in other regions inside the patient's body or is positioned/secured onto, or otherwise located outside of, the patient's body.

Figure 2:
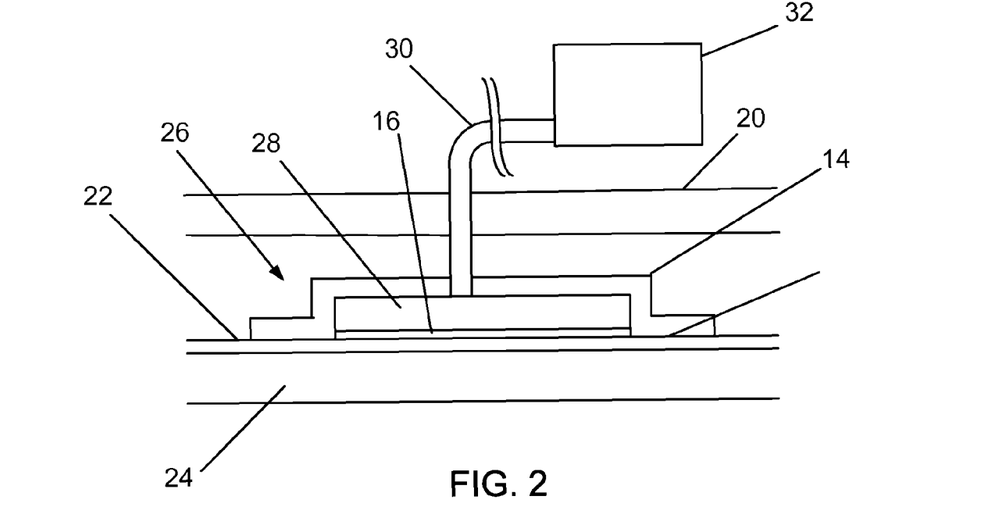
FIG. 2 is a side section view, illustrating an embodiment of the drug delivery system including an epicardial patch placed on an epicardial surface with a remote reservoir that may be provided external to the patient or implanted subcutaneously.

FIG. 2 illustrates a drug delivery device which includes an epicardial patch 26 placed on an epicardial surface 22 according to one or more embodiments of the present invention. The epicardial patch 26 includes a first drug reservoir 28 for containing a volume of a drug between a backing layer 14 and a diffusion control layer 16. The epicardial patch 26 is fluidly connected to a second drug reservoir 32 of a reservoir device via a catheter 30. The catheter 30 passes through the pericardium 20 and feeds the drug contained in the second reservoir 32 into the first reservoir 28 of the epicardial patch 26. The reservoir device containing the second drug reservoir 32 may be implantable.

In an alternative embodiment, the first reservoir is omitted from, or has a tiny volume in, the epicardial patch, so that essentially all of the drug released from the patch is delivered to the patch from the second (i.e., the remote) reservoir.

In open surgical applications, the pericardium may be opened by the surgeon and the epicardial patch 10 or 26 may be placed directly onto the heart. In minimally invasive applications, the pericardial space can be accessed for initial deployment of the epicardial patch 10 or 26 in various ways. For example, a guide wire may be inserted into the pericardial space through a subxiphoid percutaneous needle. Alternatively, a guide wire may be inserted into the pericardial space through a remote venous sheath (e.g., femoral or subclavian) and advanced across a right atrial puncture into the pericardial sac. The epicardial patch 10 or 26 may then be deployed over the guide wire.

For applications in which a second drug reservoir 32 is used, the catheter 30 may be attached on one end to the patch and the free end can be tunneled to an indwelling chamber, much as pacemakers are inserted. For applications in which the second drug reservoir 32 is maintained outside the patient's body, the catheter 30 may be tunneled out of the body, much like an external pacing lead or a chest drainage tube.

The patch optionally includes a pump unit to assist with the administration of the inotropic agent and/or to assist with refilling of the drug reservoir of the patch. Non-limiting examples of pumps that are suitable for use in embodiments include osmotic pumps, electroosmotic pumps, vapor pressure pumps, electrolytic pumps, effervescent pumps, piezoelectric pumps, hydrolytic systems, and the like. In one embodiment, the drug delivery patch includes a mechanical or electromechanical infusion pump. Non-limiting examples of such devices include those described in U.S. Pat. Nos. 4,692,147; 4,360,019; 4,487,603; and 4,725,852. In one embodiment, the drug delivery patch comprises an osmotically-driven pump. Non-limiting examples of osmotic-driven devices include U.S. Pat. Nos. 3,760,984; 3,845,770; 3,916,899; 3,987,790; 3,995,631; 3,916,899; 4,016,880; 4,036,228; 4,111,202; 4,111,203; 4,203,440; 4,203,442; 4,210,139; 4,327,725; 5,726,850; 4,865,845; 5,057,318; 5,059,428; 5,112,614; 5,137,727; 5,234,692; 5,234,693; and 5,728,396.

(iii) The Adhesive Layer or Attachment Element

In one embodiment, the patch comprises an adhesive layer for selectively adhering the patch to a surface of the heart. The adhesive layer may be in any suitable configuration for affixing the patch to the epicardial surface. For example, the adhesive portion may completely or partially surround the edge of the patch in its entirety or one or more layers of the patch (i.e., the drug delivery layer, diffusion controlling layer, or backing layer). Still further, the adhesive portion may comprise tissue adhesive in single or multiple discreet areas or locations, or may be configured in a continuous manner, such as a ring, a rectangle, or some variation thereof.

Tissue adhesives are known in the art, any of which may be used to secure the patch provided herein so long as it does not substantially impair muscle structure or function or the rate of drug delivery. See, e.g., U.S. Pat. Nos. 6,034,140; 5,985,312; 5,292,362; and 5,290,552, the contents of which are incorporated herein by reference for their teachings regarding tissue adhesives. Non-limiting examples of suitable bioadhesives include BioGlue™ (CryoLife, Inc.), fibrin-, fibrinogen-, and thrombin-based sealants, bioactive ceramic-based sealants, and cyanocrylate sealants, including, but not limited to, Vitex (V.I. Technologies, NY), Quixil (Omrix Biopharm SA, Brussels), Tisseel (Baxter International, Deerfield, Ill.), Hemaseel APR (Haemacure, Sarasota, Fla.), PlasmaSeal (Plasmaseal, San Francisco, Calif.), AutoSeal (Harvest Technologies, Norwell, Mass.), Floseal (Fusion Medical Technologies, Mountain View, Calif.), Bioglass (U.S. Biomaterials, Alachua, Fla.), and CoStasis (Cohesion Technologies).

In one embodiment, the tissue adhesive comprises a bioresorbable adhesive. Bioresorbable adhesives may be formed by forming intermacromolecular complexes of a carboxypolysaccharide and, optionally, a poly ether, such as polyethylene oxide. The carboxypolysaccharide may be of any biocompatible sort, including but not limited to carboxymethyl cellulose 20 (CMC), carboxyethyl cellulose, chitin, hyaluronic acid, starch, glycogen, alginate, pectin, carboxymethyl dextran, carboxymethyl chitosan, and glycosaminoglycans such as heparin, heparin sulfate, and chondroitin sulfate.

In some embodiments, the patch is manufactured with an adhesive layer that is ready for attachment to the heart, i.e., the adhesive will adhere to the organ surface upon contact (e.g., the adhesive layer is a moist tissue adhesive). In some of these embodiments, the adhesive layer may be covered by a release liner, as described below. Alternatively, the patch may be manufactured dry, and, upon contact with the epicardial surface, it can hydrate and self-adhere to the epicardium.

The patch also can be affixed to the heart by means of sutures, hooks, needles and other mechanical fasteners known to those skilled in the art. Such exemplary attachment elements can be part of the drug delivery layer or the drug diffusion layer or can be a separate element.

The patch may further comprise a release liner, e.g., a strippable, protective coating that covers at least the drug-permeable and adhesive portions of the drug delivery patch. Just prior to use, the coating is peeled away from the patch, exposing either the diffusion controlling layer or drug delivery layer, and discarded. The coating may comprise the same materials as the drug delivery layer or diffusion controlling layer, with the provision that the coating is made strippable, e.g., by siliconizing.

B. The Drug Formulation

The device may be used to deliver essentially any drug, including for example small molecule drugs, proteins, and biologics. As used herein, "drug formulation" and "drug" will be used interchangeably to refer to the form of the drug, the drug itself, and other components which may be used to enhance delivery of the drug or control the rate of delivery of the drug. In an embodiment, the drug is a known drug, or drug combination, effective for treating diseases and disorders of the heart. In a particularly preferred embodiment, the drug is an inotropic agent. In another particular embodiment, the drug comprises a mixture of two or more inotropic agents, or a mixture of an inotropic agent with another drug.

(i) Inotropic Agents

As used herein, "inotropic agents" or "positive inotropic agents" or "inotropes" or "positive inotropes" will be used interchangeably and refer to the effect such agents produce, i.e. improves cardiac output by increasing the force of myocardial muscle contraction. "Positive inotropic effect" means that the contractility of the cells is enhanced in a dose-dependent manner.

Positive inotropic agents of the present invention include any agents which provide the heart with contractile support. The agent can be an inotropic agent such as a sympathomimetic agent, a phosphodiesterase inhibitor, or a calcium sensitizer as long as one obtains the desired contractile effect on the heart. Inotropic compounds include agents that interact with the sympathetic nervous system and modulate calcium entry, G-proteins, ATP and GTP. Inotropic agents also include cardiac glycosides.

Non-limiting examples of sympathomimetic compounds include epinephrine, norepinephrine, dopamine, dobutamine, dopexamine, terbutaline, and isoproterenol, and analogues and derivatives thereof. Non-limiting examples of phosphodiesterase inhibitors include milrinone, amrinone, enoximone, and pimobendan, and analogues and derivatives thereof. Non-limiting examples of calcium sensitizers include levosimendan, pimobendan, and analogues and derivatives thereof. Non-limiting examples of cardiac glycosides include digoxin, eicosanoids (such as prostaglandins), glucagon and calcium.

The dose of the positive inotropic agent is a therapeutically effective dose. In particular embodiments, the positive inotropic agent can be locally administered at a dose which produces in the patient a local effect equivalent to the systemic intravenous administration of between about 2 and about 20 mcg/kg/min. However, in other embodiments, higher and lower dosages can be administered to patients. Optimizing therapy to be effective across a broad population can be performed with a careful understanding of various factors to determine the appropriate therapeutic dose. Typically, the dose locally delivered with the present patch can be much lower than the dose administered systemically or by intravenous infusion, as illustrated in the examples set forth herein below, because the device achieves more efficient local delivery of the inotropic agents within the myocardial tissue of the heart than may be achieved by conventional means or other known drug delivery methods.

In one embodiment, a therapeutically effective dose of an inotropic agent is an amount sufficient to provide a myocardial concentration of the inotropic agent in the range of about 10 ng/ml and about 100 ng/ml while systemic concentrations of the inotropic agent in the plasma are below about 5 ng/ml.

Release characteristics of the drug may impact the design choice of drug in particular applications. Therefore, the water solubility of the drugs and their alternatives may play a role in deciding which drug to incorporate into the presently disclosed drug delivery devices. For example, the efflux rate of the drugs from the drug delivery device can be altered to achieve a desired rate of delivery using methods known to those skilled in the art, non-limiting examples of which include encapsulation of the agents in microparticles or liposomes, conjugation of the agents to macromolecules, or altering of form of the agents (i.e., from the salt to the free acid/base form).

In one embodiment, the inotropic agents are poorly soluble in water (i.e. hydrophobic). As used herein, "poorly soluble" is defined as including the following solubility classes as defined by the solubility classification of the United States Pharmacopoeia (USP 24/NF 19, effective Jan. 1, 2000; p. 2254): "slightly soluble", requiring 100 to 1000 parts of solvent to dissolve; "very slightly soluble", requiring 1000 to 10,000 parts of solvent; and "practically insoluble, or insoluble", requiring over 10,000 parts of solvent. In another embodiment, the inotropic agents are soluble in water. As used herein, "soluble" is defined by the United States Pharmacopoeia as being "very soluble," "freely soluble," "soluble," and "sparingly soluble."

(ii) Other Components

Other components also may be included in the drug formulation, in minor amounts, to impart one or more useful properties to the device.

In one embodiment, the drug formulation further comprises one or more pharmaceutically acceptable excipients known in the art. For example, the pharmaceutically acceptable excipients may be selected to increase or decrease the rate of diffusion of the drug from the drug delivery layer and/or drug reservoir.

In one embodiment, the drug formulation comprises one or more penetration enhancers (also referred to as permeation enhancers or absorption enhancers) which are capable of promoting trans-tissue penetration. Not wishing to be bound by any theory, it has been suggested that such compositions enhance penetration by enlarging the interstitial spaces between the cells of the barrier or by enhancing solubility of the drug in the barrier. Such penetration enhancers are known in the art for use in transdermal applications and are described, for example, in U.S. Patent Publication No. 2001/0039262.

C. The Device Materials

The device provided herein can be formed of any material suitable for local administration of an inotropic agent directly to the heart. Desirably, the patch and optionally other aspects of the device (i.e., catheters) comprise a polymer material. Those skilled in the art will appreciate that one or more appropriate polymers may be selected for the various components of the patch in order to achieve the desired function. For example, the backing layer comprises a polymer which is substantially impermeable to the inotropic agent while the drug delivery layer and optionally diffusion controlling layer comprise polymers which are substantially permeable to the inotropic agent.

(i) The Polymer Material

The polymer is essentially any biocompatible polymer, co-polymer, or polymer blend suitable for use in a drug delivery patch. In one aspect, the patch comprises one or more polymers. Generally, both biodegradable and non-biodegradable polymers may be used to create the patches described herein. In a preferred embodiment, the products of the polymers' degradation should not pose a health risk to the heart and cardiovascular system.

In one embodiment, the polymer of the patch is biodegradable. For example, the polymer of the patch may be poly(lactic-co-glycolic) acid ("PLGA"), polylactide; poly(orthoesters), poly(aminoesters), polyanhydrides, polyorganophosphazenes, or any combination thereof. Other biodegradable polymers known to those skilled in the art including polyethylene glycols may also be applied and selected based on the desired mechanical properties and polymer-drug interaction.

In another embodiment, the polymer of the patch is non-biodegradable. For example, the polymer may be ethyl cellulose, poly(butyl acrylate), poly(urethanes), silicone resins, nylon, ammonium polyacrylate, acrylamide copolymers, acrylate/acrylamide copolymers, acrylate/ammonium acrylate copolymers, acrylate/alkyl acrylate copolymers, acrylate/carbamate copolymers, acrylate/dimethylaminoethyl methacrylate copolymers, ammonium acrylate copolymers, styrene/acrylate copolymers, vinyl acetate/acrylate copolymers, aminomethylpropanol/acrylate/dimethylaminoethylmethacrylate copolymers, or any combination thereof. Other non-biodegradable polymers known to those skilled in the art may also be applied and selected based on the desired mechanical properties and polymer-drug interaction.

The backing layer of the patch may be made to be resistant, even if not impermeable, to release of the drug, so as to direct the drug release toward the epicardium. Such a backing layer, or barrier layer, may be formed, for example, from one or more polymers dense enough so that the diffusivity of the drug through the backing layer is sufficiently low and the path of least resistance is for the drug to be released from the patch into adjacent tissue and minimally through the backing layer. Non-limiting examples of biocompatible polymers that can be used as the barrier layer include PLA (polylactic acid), PGA (polyglycolic acid), poly($\epsilon$-caprolactone), and copolymers thereof, such as poly(L-lactic acid-co-$\epsilon$-caprolactone) or PLGA (poly(lactic acid-co-glycolic acid)). Other polymers also can be formulated to be dense, limiting permeability to small molecule drugs.

In an alternative embodiment, the polymer of the patch may be replaced or augmented with a non-polymeric material. In one embodiment, for example, the patch may include a flexible metal film in selected areas to limit the rate of drug. In one embodiment, the drug releasing side of the patch may include one or more microperforations or microslits that may serve as diffusion pathways for the drug.

(ii) Other Components

In one embodiment, plasticizers may be incorporated into the device to alter the drug release characteristics of the device and/or to alter the flexibility of the patch (e.g., to enhance its conformability to and movement with the heart). As used herein, the plasticizer is any suitable material known in the art that can be blended with the polymer (e.g., the polymer of the drug-polymer film) to increase its mechanical flexibility. Plasticizers may also affect the drugs' incorporation into the polymer of the drug-polymer film and release kinetics. Any biocompatible plasticizer known in the art may be used. Examples of plasticizers include compounds of the pluronic/poloxamer non-ionic surfactant family and lipids. Particular plasticizers that may be used include Span 20, Tween 20, propylene glycol, or combinations thereof. Other components also may be included in the device, either in the reservoir material, the patch material, or the drug formulation itself, in minor amounts to impart one or more useful properties to the device.

II. Methods of Using the Device/Applications

In another aspect, a method is provided for administering one or more drugs to the heart of a patient in need thereof. Generally described, the method includes implanting an inotropic agent delivery patch onto the epicardial surface of a heart, where the patch comprises (i) a backing layer that is substantially impermeable to at least one inotropic agent; (ii) a drug delivery layer proximate the backing layer; and (iii) a drug reservoir located between the backing and drug delivery layers. The drug reservoir contains at least one inotropic agent, which may be loaded into the reservoir before or after implantation. Desirably, the patch is operable to deliver at least one inotropic agent to the myocardium via the epicardium without substantially violating muscle structure or muscle function.

The patch may be applied to the epicardium using techniques known to those skilled in the art. For example, in one embodiment the patch may be applied directly to the epicardium during surgical procedures in which there is a surgical field exposure. In one embodiment the patch may be applied directly to the epicardium using minimally invasive procedures, for example through a pericardial window. In still another embodiment, the patch may be applied directly to the epicardium percutaneously, or via endovascular catheters.

Placement of the delivery vehicle can be understood with reference to the different compartments of the heart. The heart is subdivided by a muscular septum into two lateral halves, which are named respectively right and left. A transverse constriction subdivides each half of the heart into two cavities, or chambers. The upper chambers consist of the left and right atria, which collect blood and help fill the lower chambers. The lower chambers consist of the left and right ventricles, which pump blood to the rest of the body. The chambers are defined by the walls of the heart. The right atrium communicates with the right ventricle by the tricuspid valve. The left atrium communicates with the left ventricle by the mitral valve. The right ventricle empties into the pulmonary artery by way of the pulmonary valve. The left ventricle empties into the aorta by way of the aortic valve. The external layer of muscle surrounding all chambers of the heart is referred to as the epicardial surface.

Circulation of the heart consists of two components. First is the functional circulation of the heart, i.e., the blood flow through the heart from which blood is pumped to the lungs and the body in general. Second is the coronary circulation, i.e., the blood supply to the structures and muscles of the heart itself.

The functional circulation of the heart pumps blood to the body in general, i.e., the systemic circulation, and to the lungs for oxygenation, i.e., the pulmonic and pulmonary circulation. The left side of the heart supplies the systemic circulation while the right side of the heart supplies the lungs with blood for oxygenation. Deoxygenated blood from the systematic circulation is returned to the heart and is supplied to the right atrium by the superior and inferior venae cavae. The heart pumps the deoxygenated blood into the lungs for oxygenation by way of the main pulmonary artery. The main pulmonary artery separates into the right and left pulmonary arteries, which circulate to the right and left lungs, respectively. Oxygenated blood returns to the heart at the left atrium via four pulmonary veins. The blood then flows to the left ventricle where it is pumped into the aorta, which supplies the body with oxygenated blood.

The functional circulation supplies blood to the heart by the coronary circulation. The coronary arteries arise from the proximal aorta through the left and right coronary ostia, course along the epicardial surface of the heart, and send off numerous branches to supply the myocardium. Blood is cleared from the muscle by cardiac veins that flow into the coronary sinus and right atria. The heart wall is surrounded by a pericardial sac, which contains it within interstitial fluid.

In one embodiment, the patch loaded with the inotropic agent is placed on the epicardium of the heart, before the pericardial sac and sternum are closed, allowing direct release of the inotropic agent to the heart. In one embodiment, the patch is placed away from the sinoatrial node or the right atrium. In one embodiment, the patch is placed on the apex of the ventricle or left ventricular free wall.

EXAMPLES

The present invention is further illustrated by the following examples, which are not to be construed in any way as imposing limitations upon the scope thereof. On the contrary, it is to be clearly understood that various other embodiments, modifications, and equivalents thereof which, after reading the description therein, may suggest themselves to those skilled in the art without departing from the spirit of the present invention and the scope of the appended claims.

Example 1

A Sprague Dawley rat was anesthetized with pentobarbital and catheters were placed in the right internal jugular vein and right femoral artery for continuous pressure measurement and IV access. An arteriotomy in the right carotid artery allowed passage of a Millar (Houston, Tex.) conductance pressure-volume catheter across the aortic valve and into the left ventricle. This catheter allows measurement of indices of myocardial contractile function. A tracheotomy was performed and the animal ventilated prior to sternotomy and chest retraction.

A pericardial drug releasing platform was made from a calcium crosslinked alginate disk (6.5 mm diameter) and placed on top of the left ventricle. Dobutamine was then applied to the drug release platform for pericardial inotropic treatments. In vitro experimentation suggested that the drug was released out of the disk into the epicardial tissue at approximately 1 mcg/kg/min. In another experiment dobutamine was infused intravenously (IV) at 1 mcg/g/min and the same hemodynamic and contractile indices were continuously recorded.

Figure 3:
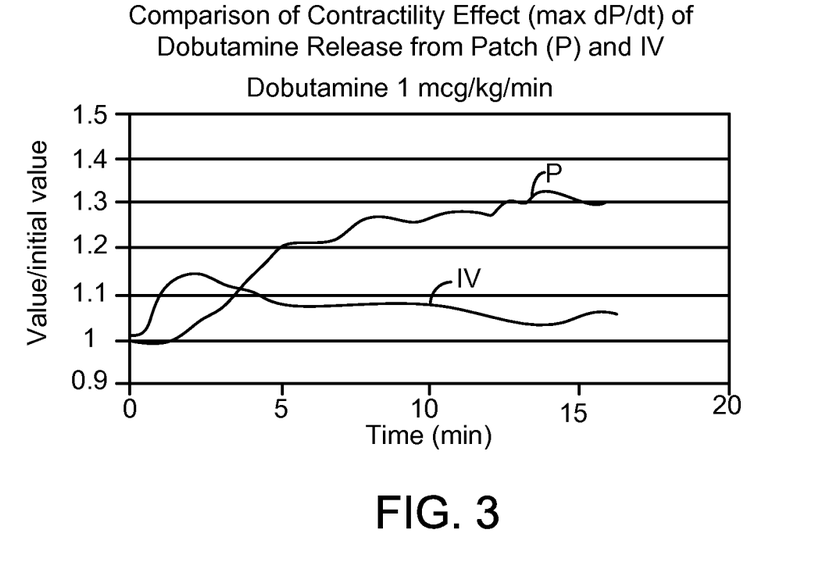
FIG. 3 is a graph of experimental data, illustrating the contractility effect (specifically, an index of contractility: maximum rate of change of pressure within the left ventricle (max dP/dt)) of dobutamine release from intravenous infusion compared to dobutamine release from one embodiment of an epicardial patch placed on an epicardial surface.

As illustrated in FIG. 3, dobutamine release at a dosage of 1 mcg/kg/min via the patch results in a greater increase in contractility of myocardial tissue which is sustained for a longer period of time than intravenous infusion of dobutamine at the same dosage.

Figure 4:
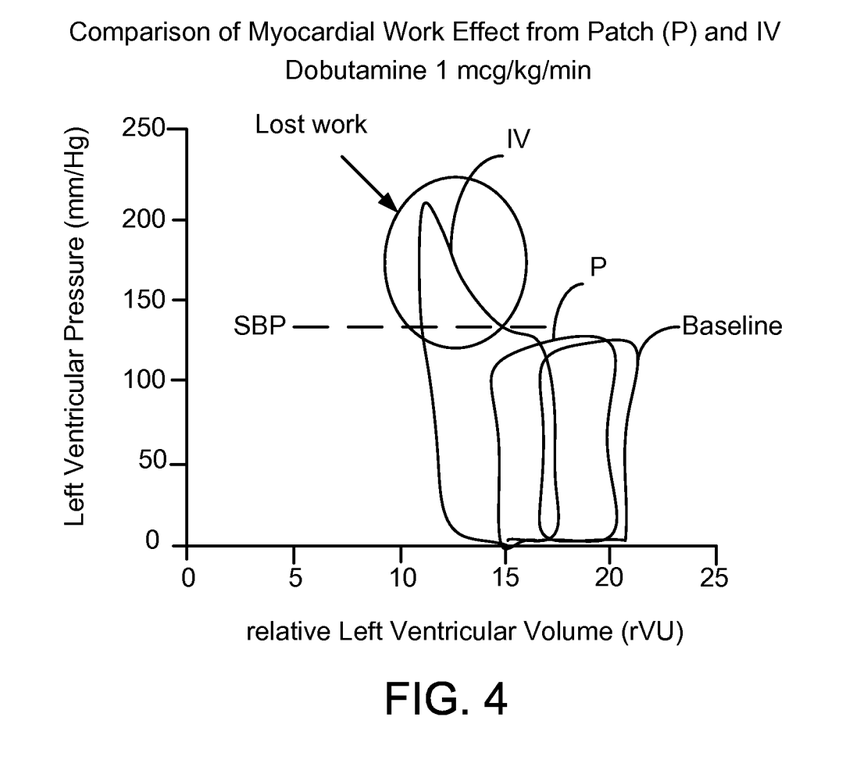
FIG. 4 is a graph of experimental data, illustrating the myocardial work effect of dobutamine release from intravenous infusion compared to dobutamine release from one embodiment of an epicardial patch placed on an epicardial surface. The area inside each of these pressure-volume loops is the work done by the heart in one cardiac cycle.

FIG. 4 illustrates pressure volume loops of these same animals before and after inotropic drug therapy. As illustrated in FIG. 4, dobutamine release at a dosage of 1 mcg/kg/min via the patch results in a greater ventricular stroke volume and more efficient cardiac work than intravenous infusion of dobutamine at the same dosage. As has been observed with IV infusion of other $\beta_1$ agonists, venodilation reduces end-diastolic volume, arterial dilation decreases end-systolic volume, and ventricular pressure rises late in systolic ejection. Thus, while IV inotropes may increase contractility, they do so by greatly increasing myocardial stroke work (SW) as measured by the area inside the PV loop. In contrast, patch delivery is more gentle, localized, and without direct vascular effects or changes in loading conditions. There is marked reduction in end-systolic volume reflecting higher contractile states with no increase in LV pressure during ejection, minimal change in diastolic filling, and minimal increase in SW. These differences in PV loop morphology indicate that the route of delivery has a profound effect on the mechanism of the hemodynamic response.

Figure 5:
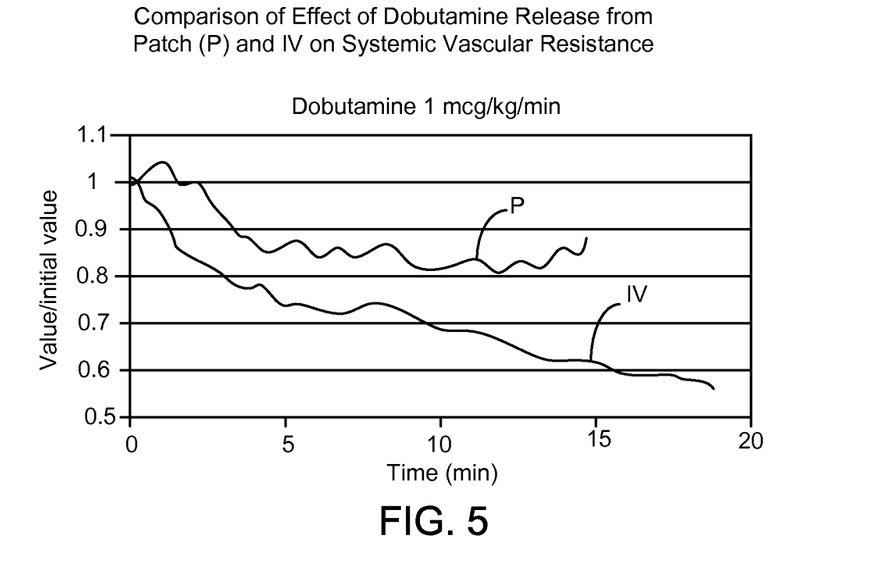
FIG. 5 is a graph of experimental data, illustrating the effect of dobutamine release from IV infusion on Systemic Vascular Resistance in comparison with effect of dobutamine release from one embodiment of an epicardial patch placed on an epicardial surface.
Figure 6:
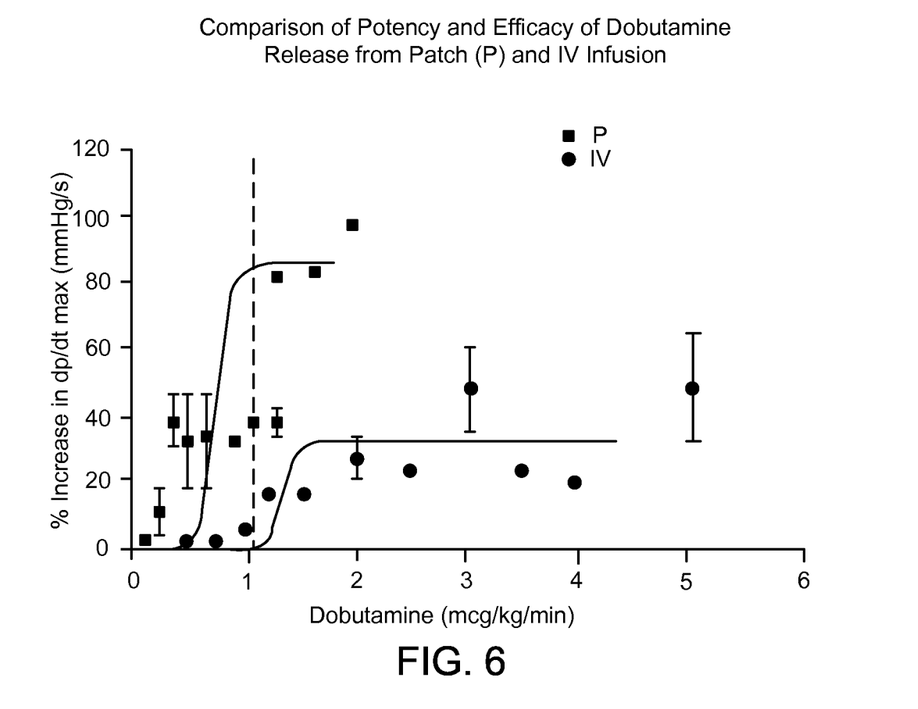
FIG. 6 is a graph of experimental data, illustrating the potency and effect on contractility of dobutamine release from intravenous infusion compared to dobutamine release from one embodiment of an epicardial patch placed on an epicardial surface.

As illustrated in FIG. 5, dobutamine release at a dosage of 1 mcg/kg/min via intravenous infusion excessively decreases systemic vascular resistance, whereas dobutamine release of the same dosage via the patch demonstrates an only minimal effect. As illustrated in FIG. 6, dobutamine release via the patch is more potent and efficacious than intravenous infusion of dobutamine. Dobutamine release via the patch results in a larger increase in contractility with a smaller dose than intravenous infusion of dobutamine.

Example 2

Hannaford swine (15-25 weeks old, 45-60 kg) were fasted overnight but given full access to water. Telazol (2 mg/kg IM at a ratio of zolazepam:tiletamine of 1:1) was given IM for sedation. Anesthesia was induced with inhaled isoflurane 2% prior to tracheal intubation (9.0 cuffed). A 22 gauge peripheral IV was inserted into an ear vein for drug administration and volume resuscitation (Ringer's lactate 4 ml/kg/hr). Anesthesia was maintained during surgical preparation with isoflurane 2% in oxygen. Respiratory rate was be fixed to 10 breaths per minute and the tidal volume adjusted between 6 and 10 ml/kg to maintain expired end-tidal carbon dioxide between 35 and 40 mmHg. Inhaled isoflurane was discontinued after surgical preparation, and balanced total intravenous anesthesia was initiated with pentobarbital (10 mg/kg/hr) and pancuronium (0.5 mcg/kg/hr) prior to experimentation.

Vascular access introducer sheaths (7 FR) were placed in a femoral vein, the right internal jugular vein and both femoral arteries using a Seldinger technique under ultrasound guidance. A balloon tipped pulmonary artery catheter was inserted through the right internal jugular venous sheath and into the pulmonary artery to allow measurement of central venous pressure (CVP), pulmonary artery pressures, and thermodilution cardiac output. Heparin 5000 units was given to keep activated clotting time above 250 seconds. A pig-tail Millar conductance catheter was advanced retrograde across the aortic valve from the right femoral arterial sheath, and allows instantaneous recordings of the pressure and volume within the left ventricle. Following midline sternotomy the pericardium was retracted. Excess Ringer's lactate solution was given to replace blood losses and maintain CVP greater than 8 mm Hg. Continuous hemodynamic measurements were taken including heart rate (HR), mean arterial pressure (MAP), central venous pressure (CVP), contractility (max dP/dt), systemic vascular resistance (SVR), stroke volume (SV), cardiac output (CO) and stroke work (SW).

Figure 7:
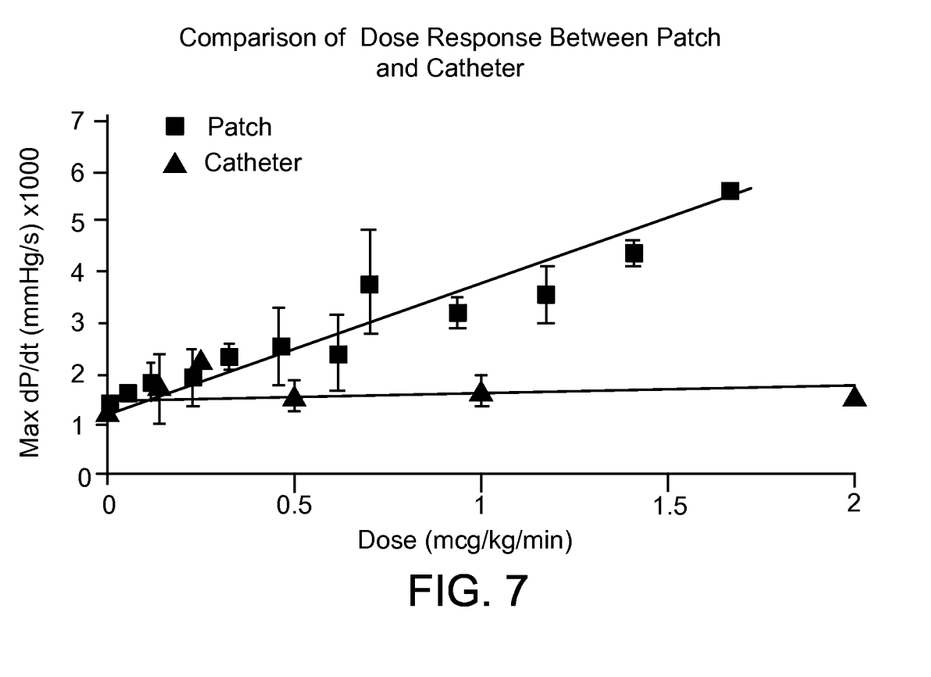
FIG. 7 is a graph of experimental data, comparing dose response of dobutamine released from a catheter placed inside the pericardial sac in comparison with dobutamine released from one embodiment of an epicardial patch placed on an epicardial surface.

A pericardial drug releasing platform was constructed from 2 calcium crosslinked alginate disks which were sealed around the edges with GluStitch and formed a bladder for pericardial drug. A catheter was placed into the bladder formed by the two disks and allowed continuous infusion of inotropic drug into the pericardial fluid. This device spread drug over the surface of the heart at a controllable rate of delivery. In another experiment, dobutamine was introduced into the pericardial sac through a catheter without the use of the patch. As illustrated in FIG. 7, dobutamine release via the patch results in a greater increase in myocardial contractility than dobutamine release via the catheter.

Figure 8:
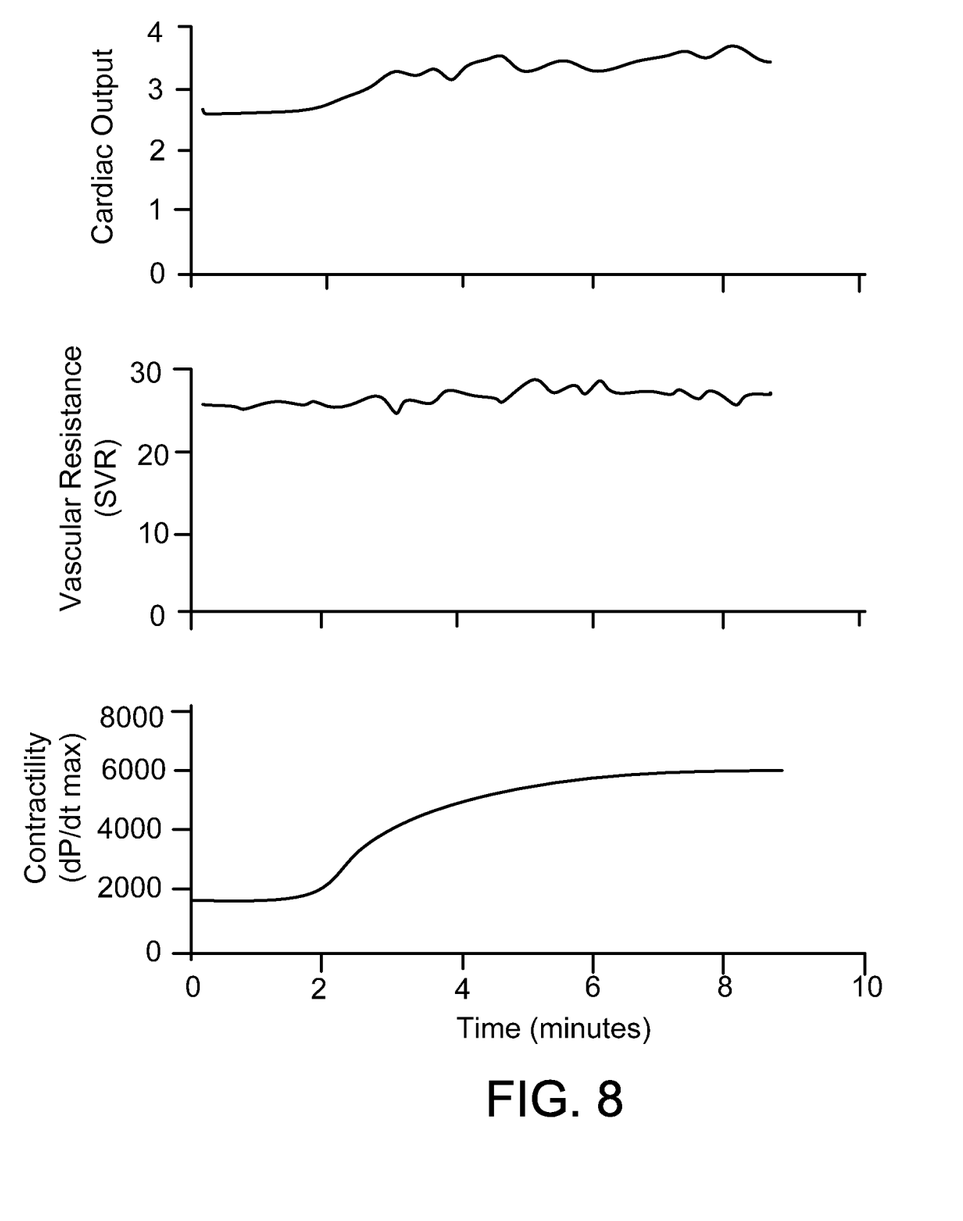
FIG. 8 is a series of graphs of experimental data, illustrating the efficacy of dobutamine released from one embodiment of an epicardial patch placed on an epicardial surface of swine to increase contractility and cardiac output without lowering systemic vascular resistance.
Figure 9:
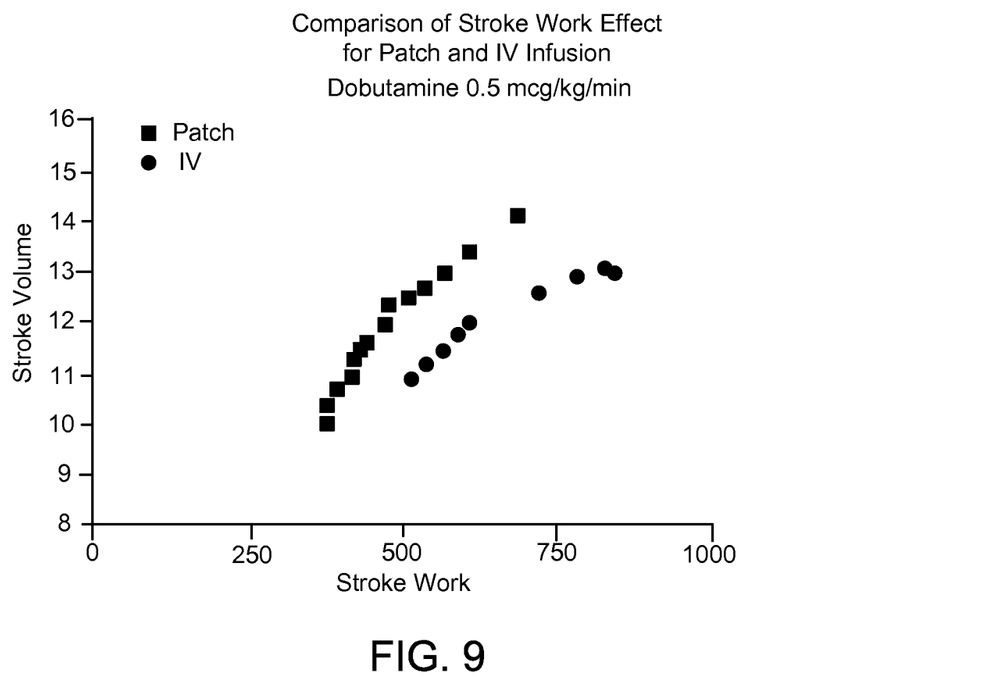
FIG. 9 is a graph of experimental data, illustrating the stroke work effect of dobutamine release from intravenous infusion compared to dobutamine release from one embodiment of an epicardial patch placed on an epicardial surface.

In yet another experiment, dobutamine was introduced intravenously. As illustrated in FIG. 8, dobutamine release via the patch results in increased contractility and cardiac output without significantly reducing systemic vascular resistance. These data show that the time response of increasing contractility is very rapid after pericardial application. As illustrated in FIG. 9, dobutamine release at a dosage of 0.5 mcg/kg/min via the patch results in less stroke work per stroke volume than intravenous infusion of dobutamine at the same dosage.

Figure 10:
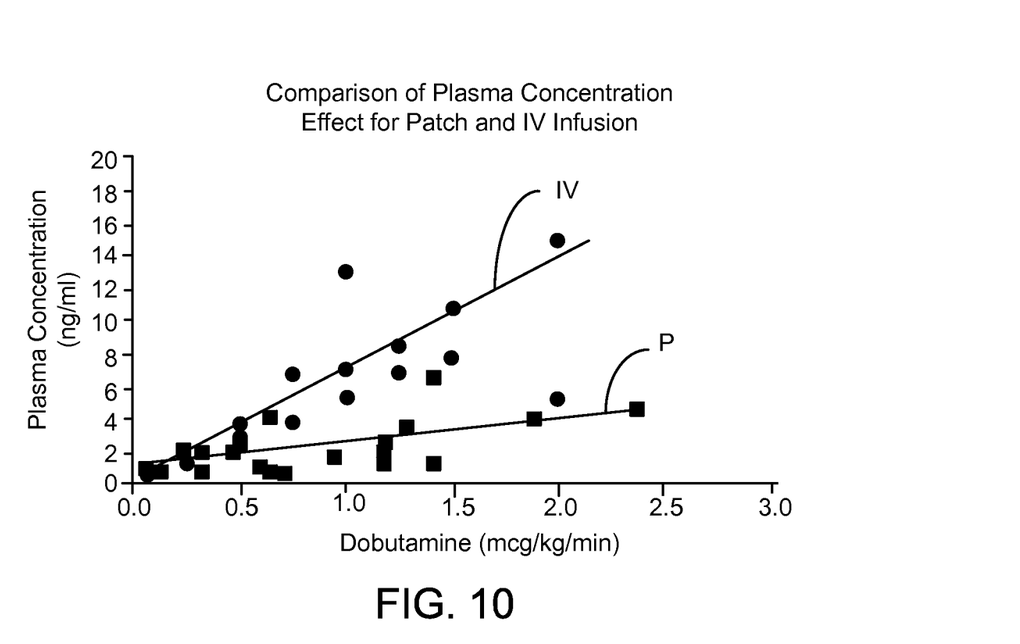
FIG. 10 is a graph of experimental data, illustrating the plasma concentration of dobutamine following intravenous infusion compared to dobutamine release from one embodiment of an epicardial patch placed on an epicardial surface.

Arterial blood samples were taken for measurement of plasma dobutamine levels. As illustrated in FIG. 10, dobutamine release via intravenous infusion results in substantially higher myocardial plasma concentrations than dobutamine release via the patch. These data show that the plasma drug levels are lower following pericardial delivery than IV delivery, indicating that patch application was truly local.

Figure 11:
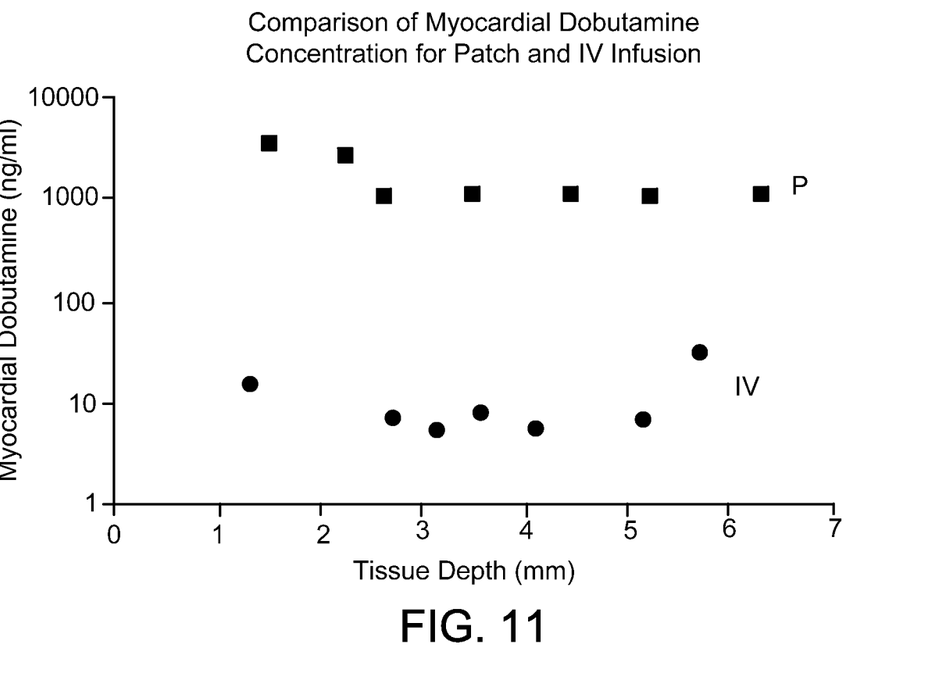
FIG. 11 is a graph of experimental data, comparing the myocardial dobutamine concentration following intravenous infusion compared to dobutamine release from one embodiment of an epicardial patch placed on an epicardial surface.

The heart was arrested with a large potassium IV bolus and removed. A core of tissue from under the device was taken for measurement of drug levels within the myocardium. As illustrated in FIG. 11, dobutamine release via the patch results in myocardial dobutamine concentrations which are orders of magnitude higher at all tissue depths than intravenous infusion of dobutamine at the same dosage. This data indicates that local delivery via the patch may load the heart with drug to much higher levels than could be obtained with IV infusion.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

We claim:

1. A preformed epicardial patch for delivery of a positive inotropic agent to the heart of a patient, comprising:
   a backing layer which is substantially impermeable to the positive inotropic agent; and
   a drug release layer attached to the backing layer and comprising the positive inotropic agent and a polymeric membrane material, which, upon placement of the epicardial patch onto a portion of the epicardial surface of the heart, the polymeric membrane material comprising a diffusion-controlling material configured to provide controlled release of the positive inotropic agent to the epicardium to a region of the myocardium and in an amount effective to increase contractility by providing a myocardial concentration of the positive inotropic agent in the range of 10 ng/ml to 100 ng/ml while maintaining plasma concentrations of the inotropic agent below 5 ng/ml,
   wherein at least one of the backing layer or the drug release layer comprises a tissue coupling portion for affixing the epicardial patch to an area of the epicardial surface, and
   wherein the epicardial patch is dimensioned and compliant to avoid impeding myocardial functionality when affixed to the area of the epicardial surface, the epicardial patch having a surface area of at least 12 cm$^2$.

2. The patch of claim 1, wherein, upon the placement of the epicardial patch onto the portion of the epicardial surface of the heart, the epicardial patch is configured to restrict the release of the inotropic agent from the drug release layer such that only a unidirectional release of the inotropic agent from the drug release layer is permitted, wherein the direction of the unidirectional release is toward the region of the myocardium.

3. The patch of claim 1, wherein the positive inotropic agent and the polymeric membrane material are combined in the drug release layer a monolithic, matrix form.

4. The patch of claim 1, wherein the positive inotropic agent in the drug release layer is disposed in at least one discrete reservoir defined between the backing layer and the polymeric membrane material.

5. The patch of claim 4, wherein the discrete reservoir is fillable, or refillable, after affixation to the epicardial surface.

6. The patch of claim 1, which resorbable in vivo.

7. The patch of claim 1, wherein the positive inotropic agent comprises a sympathomimetic agent, a phosphodiesterase inhibitor, a calcium sensitizer, or a combination thereof.

8. The patch of claim 7, wherein the sympathomimetic agent is selected from the group consisting of epinephrine, norepinephrine, dobutamine, isoproterenol, salbutamol, salmeterol, terbutaline, phenylephrine, ephedrine, clonidine, dopamine, and any combination thereof.

9. The patch of claim 7, wherein the phosphodiesterase inhibitor is selected from the group consisting of milrinone, enoximone, amrinone, and any combination thereof.

10. The patch of claim 7, wherein the calcium sensitizer is selected from the group consisting of levosimendan, pimobendan, and any combination thereof.

11. The patch of claim 1, wherein the polymeric membrane material comprises a hydrogel.

12. The patch of claim 1, wherein the polymeric membrane material comprises a poly(lactic-co-glycolic) acid, a polylactide, a poly(orthoester), a poly(aminoester), a polyanhydride, a polyorganophosphazene, a polyacrylate, a poly(ethylene glycol), or a combination thereof.

13. The patch of claim 1, wherein the polymeric membrane material comprises micro-perforations.

14. The patch of claim 1, wherein said release is zero-order over the period of release.

15. The patch of claim 1, wherein:
   the positive inotropic agent comprises dobutamine, and
   the epicardial patch is configured and dimensioned to cover a sufficient area of the epicardial surface of the heart to deliver a therapeutically effective amount of the dobutamine to the myocardiwn at a released dose of 0.5 to 1.0 mcg/kg/min.

16. The patch of claim 1, wherein:

the positive inotropic agent comprises dobutamaine, and the epicardial patch is configured and dimensioned to cover a sufficient area of the epicardial surface of the heart to increase myocardial contractility by at least 50% at a released dose of 0.5 to 1.0 mcg/kg/min dobutamine.

17. The patch of claim 1, wherein:

the positive inotropic agent comprises levosimendan, and the epicardial patch is configured and dimensioned to cover a sufficient area of the epicardial surface of the heart to deliver a therapeutically effective amount of the levosimendan to the myocardium at a released dose of about 0.05 mcg/kg/min.

18. The patch of claim 1, wherein:

the positive inotropic agent comprises levosimendan, and the epicardial patch is configured and dimensioned to cover a sufficient area of the epicardial surface of the heart to increase myocardial contractility by at least 50% at a released dose of about 0.05 mcg/kg/min levosimendan.

19. The patch of claim 1, wherein:

the positive inotropic agent comprises milrinone, and the epicardial patch is configured and dimensioned to cover a sufficient area of the epicardial surface of the heart to deliver a therapeutically effective amount of the milrinone to the myocardium at a. released dose of about 0.1 mcg/kg/min.

20. The patch of claim 1, wherein:

the positive inotropic agent comprises milrinone, and the epicardial patch is configured and dimensioned to cover a sufficient area of the epicardial surface of the heart to increase myocardial contractility by at least 50% at a released dose of about 0.1 mcg/kg/min milrinone.

21. The patch of claim 1, wherein the epicardial patch has a thickness from 0.5 mm to 5 mm.

22. The patch of claim 1, wherein the epicardial patch is in the form of a sleeve configured to cover from 80% to 100% of the ventricular epicardial surface.

23. A method of administering a positive inotropic agent to a heart of a patient in need thereof comprising:

providing an implantable epicardial patch which is affixable to an area of an epicardial surface of the heart, the epicardial patch comprising (i) a backing layer which is impermeable to the positive inotropic agent, and (ii) a drug release layer attached to the backing layer, wherein the drug release layer comprises the positive inotropic agent and a polymeric membrane material;

placing the epicardial patch onto a portion of the epicardial surface of the heart; and providing via the polymeric membrane material controlled release of the positive inotropic agent from the epicardial patch to the epicardium to a region of the myocardium in an amount effective to increase contractility by providing a myocardial concentration of the positive inotropic agent in the range of 10 ng/ml to 100 ng/ml while maintaining plasma concentrations of the inotropic agent below 5 ng/ml.

24. The method of claim 23, wherein the patch is applied directly to the epicardium percutaneously, via an endovascular catheter, or via a pericardial window or subxiphoid approach.

\* \* \* \* \*

UNITED STATES PATENT AND TRADEMARK OFFICE
CERTIFICATE OF CORRECTION

PATENT NO. : 8,562,586 B2  
APPLICATION NO. : 12/547959  
DATED : October 22, 2013  
INVENTOR(S) : Mark Lovich et al.

Page 1 of 1

It is certified that error appears in the above-identified patent and that said Letters Patent is hereby corrected as shown below:

In the Claims

In Column 16, Line 25, after "layer" insert --in--.

Signed and Sealed this  
Twenty-eighth Day of January, 2014

Michelle K. Lee  
*Deputy Director of the United States Patent and Trademark Office*